(12) United States Patent
Bingel

(10) Patent No.: US 6,346,635 B1
(45) Date of Patent: Feb. 12, 2002

(54) PREPARATION OF SILYL-BRIDGED FLUORENYL-CYCLOPENTADIENYL LIGANDS AND SILYL-BRIDGED FLUORENYL-CYCLOPENTADIENYL METALLOCENES

(75) Inventor: Carsten Bingel, Kriftel (DE)

(73) Assignee: Basell Polyolefine GmbH, Kehl (DE)

( * ) Notice: Subject to any disclaimer, the term of this patent is extended or adjusted under 35 U.S.C. 154(b) by 0 days.

(21) Appl. No.: 09/552,816

(22) Filed: Apr. 20, 2000

(30) Foreign Application Priority Data

Apr. 22, 1999 (DE) .......... 199 18 310
Jul. 15, 1999 (DE) .......... 199 33 068

(51) Int. Cl.$^7$ .................. C07F 7/08
(52) U.S. Cl. .................. 556/11
(58) Field of Search .................. 556/11

(56) References Cited

U.S. PATENT DOCUMENTS 6,114,555 A * 9/2000 Llinas et al. .......... 556/11
6,218,557 B1 * 4/2001 Blakenship .......... 556/11

\* cited by examiner

*Primary Examiner*—Paul F. Shaver
(74) *Attorney, Agent, or Firm*—Keil & Weinkauf

(57) ABSTRACT

A simplified process for the industrial preparation of silyl-bridged fluorenyl-cyclopentadienyl ligands and also a process for preparing silyl-bridged fluorenyl-cyclopentadienyl metallocenes are described.

10 Claims, No Drawings

PREPARATION OF SILYL-BRIDGED FLUORENYL-CYCLOPENTADIENYL LIGANDS AND SILYL-BRIDGED FLUORENYL-CYCLOPENTADIENYL METALLOCENES

The present invention relates to a simple process for the industrial preparation of silyl-bridged fluorenyl-cyclopentadienyl ligands and also to a process for preparing silyl-bridged fluorenyl-cyclopentadienyl metallocenes.

The metallocenes of transition group IV of the Periodic Table, i.e. the metallocenes of titanium, zirconium and hafnium, have in recent years proven to be an important consitutent of a significant new class of polyolefin catalysts (H.-H. Brintzinger, D. Fischer, R. Mülhaupt, B. Rieger and R. Waymouth, Angew. Chem. Int. Ed. Engl., 34 (1995) 1143; M. Aulbach and F. Küber, Chiuz, 28 (1994) 197). The metallocenes are, if appropriate in combination with one or more cocatalysts, used as catalyst component for the polymerization and copolymerization of olefins. Bridged metallocenes, known as ansa metallocenes, play an important role in, for example, the stereoselective preparation of polypropylene. Thus, for example, syndiotactic polypropylene can be prepared using bridged fluorenyl-cyclopentadienyl metallocenes (J. A. Ewen, R. L. Jones and A. Razavi, J. Am. Chem. Soc., 110 (1988) 6255).

The synthesis of silicon-bridged fluorenyl-cyclopentadienyl metallocenes and the use of these compounds in the polymerization of olefins is known (K. Patsidis, H. G. Alt, W. Milius and S. J. Palackal, J. Organomet. Chem., 509 (1996) 63–71; W. Spaleck, M. Aulbach, B. Bachmann, F. Kuber and A. Winter, Macromol. Symp. 89 (1995) 237–247; U.S. Pat. No. 5401817; U.S. Pat No. 5393911; EP 0628577). The synthesis of the silicon-bridged fluorenyl-cyclopentadienyl metallocenes is carried out as shown in the scheme below using a zirconocene as an example:

Scheme 1

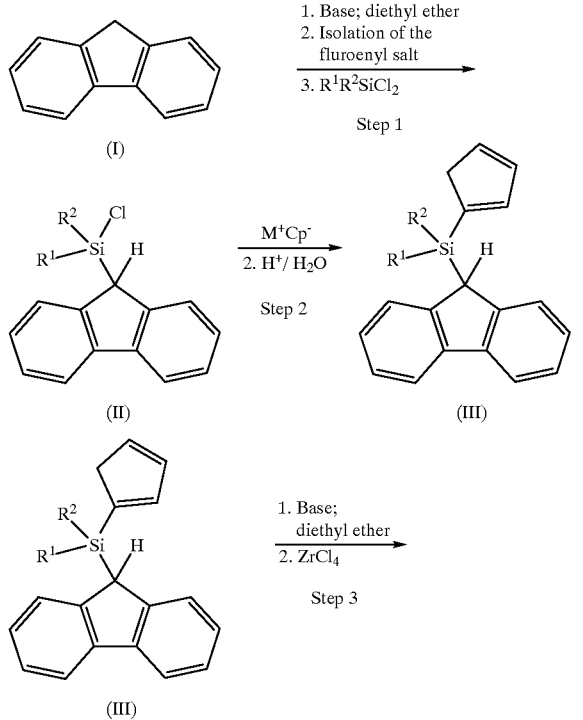

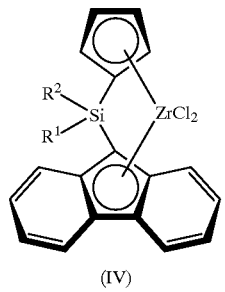

where $R^1$, $R^2$ are identical or different alkyl or aryl radicals and M can be Li, Na, MgCl or MgBr and Cp is cyclopentadiene.

A disadvantage of the syntheses described in the literature with regard to transfer to the production scale is the use of critical solvents such as diethyl ether (highly flammable) or hexamethylphosphoramide (carcinogenic). Furthermore, the isolation of fluorenyl lithium or the isolation of the dilithium salt of the silyl-bridged fluorenyl-cyclopentadienyl ligand is a complicated step in process engineering terms.

Chromatographic purification of intermediates is also a great disadvantage on the industrial scale.

It is an object of the present invention to find methods for steps 1 to 3 in Scheme 1 which avoid the abovementioned disadvantages and can be carried out without problems under industrial conditions.

We have found that this object is achieved by carrying out steps 1–3 of the above scheme (Scheme 1) using particular solvents or solvent mixtures and a particular reaction methodology, thus enabling the steps to be carried out under conditions which are feasible in process engineering terms and are acceptable in terms of safety.

The present invention accordingly provides a process for preparing compounds of the formula (IV)

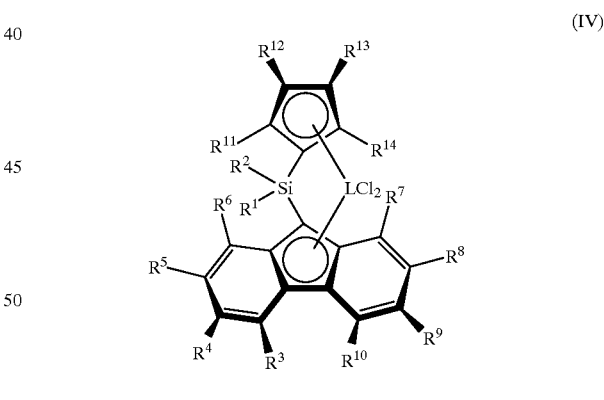

wherein
$R^1$, $R^2$ are identical or different $C_1$–$C_{20}$-hydrocarbon radicals, preferably $C_1$–$C_{10}$-alkyl or $C_6$–$C_{14}$-aryl radicals, particularly preferably methyl, ethyl, tert-butyl or phenyl,
$R^3$, $R^4$, $R^5$, $R^6$, $R^7$, $R^8$, $R^9$, $R^{10}$ are identical or different and are each hydrogen, halogen or a $C_1$–$C_{20}$-hydrocarbon radical, preferably hydrogen, $C_1$–$C_{10}$-alkyl, $C_1$–$C_{10}$-alkenyl, $C_6$–$C_{14}$-aryl, $C_7$–$C_{12}$-alkylaryl or $C_7$–$C_{12}$-arylalkyl, particularly preferably hydrogen, methyl, ethyl, propyl, isopropyl, n-butyl, tert-butyl, amyl, hexyl, heptyl, octyl or phenyl, where preferably at least $R^4$, $R^7$, $R^9$ and $R^{10}$ are hydrogen, $R^{11}, R^{12}, R^{13}, R^{14}$ are identical or different and are each hydrogen or a $C_1$–$C_{20}$-hydrocarbon radical, preferably hydrogen, $C_1$–$C_{10}$-alkyl, $C_1$–$C_{10}$-alkenyl, $C_6$–$C_{14}$-aryl, $C_7$–$C_{12}$-alkylaryl or $C_7$–$C_{19}$-arylalkyl, particularly preferably hydrogen, methyl, ethyl, propyl, isopropyl, n-butyl, tert-butyl, amyl, hexyl, heptyl, octyl, trimethylsilyl, triphenyl-methyl, 2-methyl-2-phenylpropyl, 2,2-diphenylpropyl, 2,2-diphenylethyl or phenyl, where preferably at least two of the radicals $R^{11}, R^{12}, R^{13}$ and $R^{14}$ are hydrogen and L is zirconium, hafnium or titanium, comprising the measures:

a) deprotonation of the compound of the formula (I)

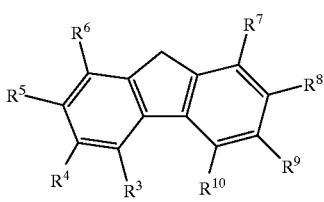

(I)

using a base, b) reaction of the deprotonated compound from step a) with $R^1R^2SiCl_2$ to give the compound of the formula (II)

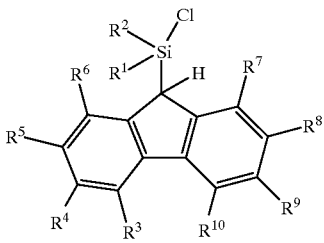

(II)

where $R^1, R^2, R^3, R^4, R^5, R^6, R^7, R^8, R^9$ and $R^{10}$ are as defined above, c) reaction of the compound of the formula (II) obtained as described in step b) with $M^+Cp^-$ to form the compound of the formula (III)

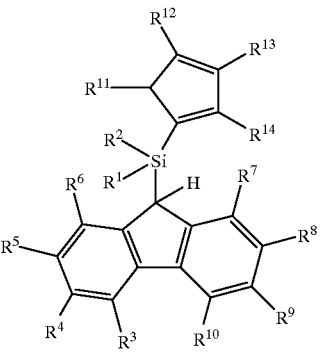

(III)

where $R^1, R^2, R^3, R^4, R^5, R^6, R^7, R^8, R^9, R^{10}, R^{11}, R^{12}, R^{13}$ and $R^{14}$ are as defined above, M is Li, Na, K, MgCl or MgBr and Cp is a substituted or unsubstituted cyclopentadienyl radical, d) reaction of the compound of the formula (III) with a base and addition of $LCl_4$, where L is zirconium, titanium or hafnium, to form the compound of the formula (IV), wherein i. the deprotonation of step a) is carried out in a mixture of one or more aromatic, aliphatic hydrocarbons and α,β-dialkoxyalkanes or α,β-dialkoxyaromatics, ii. an alkane is added after deprotonation is complete and before the reaction with the organochlorosilane as described in step b), iii. the reaction of step d) is carried out in a mixture of one or more aromatic, aliphatic hydrocarbons and a polar aprotic solvent, with the exception of diethyl ether.

In step a), the compound of the formula (I), for example fluorene, is deprotonated in an inert solvent mixture by means of a strong base, for example butyllithium, and the metal salt formed is subsequently, after addition of an alkane having from 5 to 30 carbon atoms, reacted directly without further isolation with a silicon dichloride reagent $R^1R^2SiCl_2$ to give the compound (II), with the compound (II) preferably being added to the metal salt (single-vessel process).

As fluorenyl compound of the formula (I), it is possible to use unsubstituted fluorene itself or monosubstituted and polysubstituted fluorenes, as described, for example, in EP 0528 287 A. Examples are 1-methylfluorene, 4-methylfluorene, 1-tert-butylfluorene, 2-ethylfluorene, 2-tert-butylfluorene, 4-tert-butylfluorene, 4-phenylfluorene, 2,7-di-tert-butyl-fluorene, 2,7-di-tert-butyl-4-methylfluorene and 2,7-di-tert-butyl-4-phenylfluorene. Furthermore, instead of substituted fluorenes, it is also possible to use the fluorene-analogous heteroatom-substituted tricyclic compounds described in WO 98/22486. Preference is given to using fluorene, 4-methyl-fluorene, 2-tert-butylfluorene, 4-tert-butylfluorene, 4-phenyl-fluorene and 2,7-di-tert-butylfluorene; very particularly preferably unsubstituted fluorene and 2,7-di-tert-butylfluorene.

In the deprotonation of step a), use is made of an inert solvent mixture of one or more hydrocarbons and one or more α,β-dialkoxyalkanes or α,β-dialkoxyaromatics.

In the process of the present invention, up to one mol of α,β-dialkoxyalkanes or α,β-dialkoxyaromatics is added per mol of fluorene, preferably less than half a mol.

The α,β-dialkoxyalkanes or α,β-dialkoxyaromatics used according to the present invention are preferably 1,2-dimethoxyethane (DME), 2,3-dimethoxybutane, 1,2-diethoxyethane, dioxane, diethylene glycol dimethyl ether, 1,2-dimethoxybenzene, 1,2-diethoxybenzene and 2-ethoxyanisole, in particular 1,2-dimethoxyethane (DME).

The hydrocarbons are aromatic and aliphatic hydrocarbons such as pentane, hexane and its isomers, heptane, ®Exxsol DSP 100–120, toluene, ethylbenzene, xylene or tetrahydronaphthalene, preferably toluene and heptane.

To suppress the formation of silyl-bridged bisfluorenylene, the silicon dichloride reagent $R^1R^2SiCl_2$ is used in excess over the metal fluorenyl salt, with the molar ratio being from 1.1:1.0 to 3.5:1, preferably from 1.25:1 to 2.5:1. The excess silicon reagent can be removed, for example by distillation or by crystallization, before addition of the $M^+Cp^-$.

The deprotonation of the compound of the formula (I), namely the fluorene, is carried out in a temperature range from −30° C. to 80° C., preferably from 20° C. to 60° C., and the subsequent reaction with the silicon reagent to form the compound of the formula (II) is carried out in a temperature range from −78° C. to 50° C., preferably from −30° C. to 30° C.

The fluorenyl-monochloro-silicon compound of the formula (II) is obtained after reaction with $R^1R^2SiCl_2$ and subsequent removal of the solvents and of excess silicon dichloride reagent $R^1R^2SiCl^2$ (step b). The possible removal of the metal chloride, for example lithium chloride, is preferably carried out prior to the removal of the solvents. The pure compound of the formula (II) can be obtained by crystallization from a hydrocarbon, preferably toluene and/or heptane.

In step c), a solution of a substituted or unsubstituted alkali metal or alkaline earth metal cyclopentadienide $M^+Cp^-$ in a cyclic or acyclic ether or polyether, with the exception of diethyl ether, is reacted with the fluorenyl-monochloro-silicon compound of the formula (II) to give the compound of the formula (III). Substituted or unsubstituted cyclopentadienes CpH can be reacted with strong bases such as sodium, potassium, sodium hydride, potassium hydride, dibutyl magnesium, butyloctylmagnesium, Grignard compounds, methyllithium or n-butyllithium to give the compounds $M^+Cp^-$. Examples of preferred substituted cyclopentadienes are methylcyclopentadiene, ethylcyclopentadiene, isopropylcyclopentadiene, tert-butylcyclopentadiene, n-butylcyclopentadiene, 1,3-n-butylmethylcyclopentadiene, 1,3-tert-butylmethylcyclopentadiene, 1,2-tert-butylmethylcyclopentadiene, 1,2-dimethylcyclopentadiene, 1,3-dimethylcyclopentadiene, 1,3-di-tert-butylcyclopentadiene and trimethylsilylcyclopentadiene.

As alkali metal or alkaline earth metal cyclopentadienide, preference is given to using sodium cyclopentadienide, which is commercially available as a solution in tetrahydrofuran (THF).

Cyclic or acyclic ethers or polyethers for the purposes of the present invention are, for example, tetrahydrofuran (THF), 2,5-dimethyltetrahydrofuran, methyl tert-butyl ether, diisopropyl ether, 1,2-dimethoxyethane (DME), 1,2-diethoxyethane, diethylene glycol dimethyl ether or tetraethylene glycol dimethyl ether. Preference is given to using THF and DME, particularly preferably THF.

When $R^1$, $R^2$ are phenyl, it is indicated in the literature (J. Organomet. Chem., 509 (1996) 64 or U.S. Pat. No. 5,393,911, column 15, lines 62, 63) that the 2nd reaction step does not function in THF. However, in agreement with W. Spaleck, M. Aulbach, B. Bachmann, F. Kuber and A. Winter, Macromol. Symp. 89 (1995) 237–247, it was able to be shown that when $R^1$, $R^2$ are phenyl, the reaction functions in THF, but the chromatographic purification described in the literature can be avoided if the process is designed appropriately.

The molar ratio of fluorenyl-monochloro-silicon compound of the formula (II) to the cyclopentadienyl anion is from 1:1 to 1:3, preferably from 1:1.5 to 1:2.5.

The reaction is carried out in the temperature range from −30° C. to 65° C., preferably from 0° C. to 40° C.

The product of the formula (III) is obtained after aqueous work-up and after removal of excess cyclopentadiene. For the further reaction, either the crude product (III) is used or (III) is crystallized from a suitable solvent or solvent mixture, for example toluene and/or heptane.

In the subsequent step d), the cyclopentadienylfluorenyl-silane (III), namely the ligand system, is doubly deprotonated in an inert solvent mixture comprising a hydrocarbon or hydrocarbon mixture and a polar aprotic solvent using a strong base, for example butyllithium, and the resulting dilithium salt of the ligand system is reacted directly, without isolation, with a titanium tetrahalide, zirconium tetrahalide or hafnium tetrahalide source to give the metallocene (IV).

The polar aprotic solvent is a cyclic or acyclic ether or polyether, with the exception of diethyl ether, or else a tertiary amine or diamine such as tetramethylethylenediamine (TMEDA). Preference is given to using 1,2-dimethoxyethane (DME) or tetrahydrofuran (THF). Preferred solvent mixtures for preparing the dilithium salt are toluene/DME and toluene/THF, particularly preferably toluene/THF.

The ratio of strong base to ligand is from 2.0:1 to 2.5:1, preferably from 2.0:1 to 2.2:1.

The ratio of the polar aprotic solvent and the strong base butyllithium is from 0.1:1 to 4:1, preferably from 0.25:1 to 2:1.

The doubly deprotonated ligand (III) is reacted with a titanium tetrahalide, zirconium tetrahalide or hafnium tetrahalide source at from −30° C. to 60° C., preferably from 0° C. to 40° C., to give the metallocene (IV).

As titanium tetrahalide, zirconium tetrahalide or hafnium tetrahalide source, preference is given to using the pure tetrachlorides or corresponding adducts of the tetrachlorides with donor solvents such as ethers or amines. Examples of adducts of the tetrahalides are: $ZrCl_4*2THF$, $ZrCl_4*DME$, $ZrCl_4*TMEDA$, $TiCl_4*2THF$, $TiCl_4*DME$, $TiCl_4*TMEDA$, $HfCl_4*2THF$, $HfCl_4*2THF$, $HfCl_4*2THF$.

Particular preference is given to the abovementioned compounds of zirconium.

The isolation and purification of the metallocene (IV) is carried out by methods known from the literature (for example: J. Organomet. Chem., 509 (1996) 63–71).

Scheme 2 below once more illustrates the individual steps of the novel process for preparing metallocenes of the formula (IV) in a preferred embodiment.

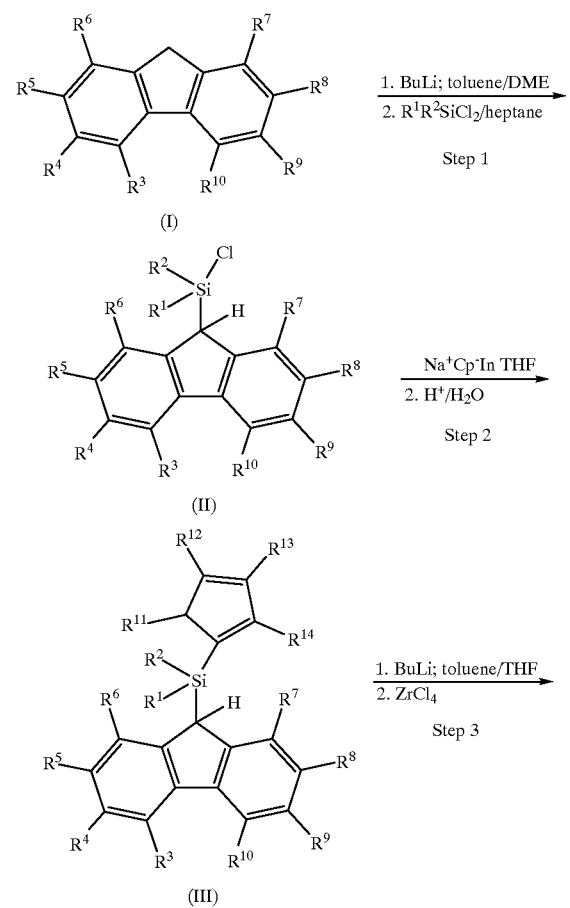

Scheme 2

-continued

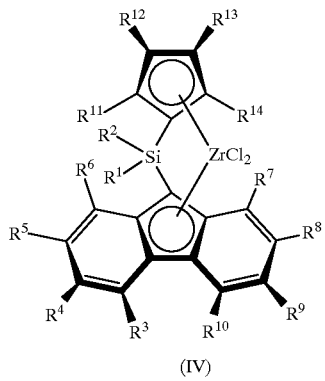

(IV)

In this scheme,

R$^1$, R$^2$ are identical or different C$_1$–C$_{20}$-hydrocarbon radicals, preferably C$_1$–C$_{10}$-alkyl or C$_6$–C$_{14}$-aryl radicals and R$^3$, R$^4$, R$^5$, R$^6$, R$^7$, R$^8$, R$^9$, R$^{10}$, R$^{11}$, R$^{12}$, R$^{13}$, R$^{14}$ are identical or different and are each hydrogen, halogen or a C$_1$–C$_{20}$-hydro-carbon radical, preferably hydrogen, C$_1$–C$_{10}$-alkyl, C$_1$–C$_{10}$-alkenyl, C$_6$–C$_{14}$-aryl, C$_7$–C$_{12}$-alkylaryl or C$_7$–C$_{19}$-arylalkyl.

Preferably, R$^1$, R$^2$ are identical or different and are each a methyl, ethyl, tert-butyl or phenyl group, and R$^3$, R$^4$, R$^5$, R$^6$, R$^7$, R$^8$, R$^9$, R$^{10}$, R$^{11}$, R$^{12}$, R$^{13}$, R$^{14}$ are identical or different and are each hydrogen, methyl, ethyl, propyl, isopropyl, n-butyl, tert-butyl, amyl, hexyl, heptyl, octyl, trimethylsilyl, triphenylmethyl, 2-methyl-2-phenylpropyl, 2,2-diphenylpropyl, 2,2-diphenylethyl or phenyl.

Very particularly preferably, R$^1$ is identical to R$^2$ and both are methyl or phenyl, R$^3$, R$^5$, R$^6$, R$^8$ are identical or different and are each hydrogen, methyl, phenyl or tert-butyl, R$^4$, R$^7$, R$^9$ and R$^{10}$ are hydrogen and R$^{11}$, R$^{12}$, R$^{13}$ and R$^{14}$ are identical or different and are each hydrogen, methyl or tert-butyl, where at least two of the radicals R$^{11}$, R$^{12}$, R$^{13}$ and R$^{14}$ are hydrogen.

The process of the present invention enables the target compound of the formula (IV) to be obtained industrially. The process of the present invention can be interrupted after any step and the intermediate can be isolated. This leads, in particular, to the process being able, for example, to be interrupted after step 2 in Scheme 2 and the compound of the formula (III) to be used as a stock compound. This process is likewise subject-matter of the invention.

The invention is illustrated by the following examples which do not, however, imply any restriction of the scope of the invention.

General procedures: the preparation and handling of air- and moisture-sensitive compounds or intermediates was carried out under an argon atmosphere (Schlenk technique). The reagents and solvents used were not purified further.

EXAMPLE 1a

1-Cyclopentadienyl-1,1-dimethyl-1-(9-fluorenyl) silane (Ia)

80 g (0.48 mol) of fluorine and 160 ml of toluene/12.8 ml (0.12 mol) of dimethoxyethane (DME) were placed in a reaction vessel and admixed with 182 ml (0.48 mol) of a 20% strength solution of butyllithium in toluene. The suspension was stirred for another 2 hours at 50° C. The suspension was diluted with 400 ml of heptane, cooled to −30° C. and added to a solution, cooled to −30° C., of 129 g (1.0 mol) of dimethyldichlorosilane in 400 ml of heptane. After stirring at room temperature for 1.5 hours, excess dimethyldichlorosilane and the solvents were removed under reduced pressure. The residue was taken up in 100 ml of THF and added at 10° C. to 480 ml (0.98 mol) of a solution of cyclopentadienylsodium in THF. The reaction mixture was stirred for another 2 hours at room temperature. 500 ml of water and 600 ml of toluene were subsequently added. After phase separation, extraction with a further 400 ml of toluene and drying over magnesium sulfate, the solvents were removed to leave 102 g of an orange oil which was about 90% of 1a according to NMR.

EXAMPLE 1b

Dimethylsilanediyl(9-fluorenyl)(cyclopentadienyl)-zirconium dichloride (1b)

16 g (50 mmol) of 1a in 250 ml of toluene/20.0 ml of DME were admixed with 39.7 ml (106 mmol) of a 20% strength solution of butyllithium in toluene and the reaction mixture was stirred at 60° C. for 1 hour. At 0° C., 12.0 g (51.5 mmol) of zirconium tetrachloride were added to the dilithium salt suspension, and the reaction mixture was stirred further at 30° C. for 1 hour. After cooling to room temperature, about ⅔ of the solvent were removed under reduced pressure, the solid was filtered off and extracted with methylene chloride. Most of the methylene chloride was evaporated on a rotary evaporator and the orange powder which precipitated was isolated by filtration and dried under reduced pressure. 13.1 g (58%) of 1b were obtained.

EXAMPLE 2a

Chlorodiphenyl-1-(9-fluorenyl)silane (2a)

80 g (0.48 mol) of fluorine and 160 ml of toluene/12.8 ml (0.12 mol) of dimethoxyethane (DME) were placed in a reaction vessel and admixed with 182 ml (0.48 mol) of a 20% strength solution of butyllithium in toluene. The suspension was stirred for another 2 hours at 50° C. The suspension was diluted with 800 ml of heptane, cooled to −10° C. and 182 g (0.72 mol) of diphenyldichlorosilane were added all at once to the suspension.

The internal temperature rose to 17° C. After stirring for 1.5 hours at room temperature, the suspension was heated to 60° C. and the lithium chloride was filtered off. After removal of the solvent, the solid which precipitated was suspended in heptane, filtered off, washed with heptane until virtually colorless and dried under reduced pressure. 136 g (73%) of 2a were obtained.

COMPARATIVE EXAMPLE 2aa

Chlorodiphenyl-1-(9-fluorenyl)silane (2a)

80 g (0.48 mol) of fluorine and 160 ml of toluene/12.8 ml (0.12 mol) of dimethoxyethane (DME) were placed in a reaction vessel and admixed with 182 ml (0.48 mo) of a 20% strength solution of butyllithium in toluene. The suspension was stirred for another 2 hours at 50° C. The suspension was diluted with 400 ml of heptane, cooled to −30° C. and added to a solution, cooled to −30° C., of 182 g (0.72 mol) of diphenyldichlorosilane in 400 ml of heptane. After stirring for 1.5 hours at room temperature, the suspension was heated to 60° C. and the lithium chloride was filtered off. After removal of the solvent, the solid which precipitated was suspended in heptane, filtered off, washed with heptane until virtually colorless and dried under reduced pressure. 123 g (66%) of 2a were obtained.

EXAMPLE 2b

1-Cyclopentadienyl-1,1-diphenyl-1-(9-fluorenyl) silane (2b)

80 g (0.21 mol) of (2a) were added at 10° C. to an about 2 molar solution of cyclopentadienylsodium in tetrahydrofuran (THF), prepared from 27.8 g (0.42 mol) of freshly cracked cyclopentadiene and 16.7 g (0.42 mol) of 60% strength sodium hydride (as an oil suspension) in 200 ml of THF and the reaction mixture was stirred at room temperature for 3 hours. 300 ml of water and 400 ml of toluene were subsequently added. After phase separation, extraction with a further 250 ml of toluene and drying over magnesium sulfate, the solvents were removed and the residue was taken up in 240 ml of n-heptane. The solid was filtered off, washed with n-heptane and dried under reduced pressure. 57 g (65%) of 2b were obtained.

EXAMPLE 2c

Diphenylsilanediyl(9-fluorenyl)(cyclopentadienyl) zirconium dichloride (2c)

20 g (48.5 mmol) of 2b in 80 ml of toluene/4.0 ml of THF were admixed with 39.7 ml (106 mmol) of a 20% strength solution of butyllithium in toluene and the yellow suspension was stirred at 60° C. for 1 hour. At 10° C., 12.0 g (51.5 mmol) of zirconium tetrachloride were added to the dilithium salt suspension and the reaction mixture was stirred further at 30° C. for 1 hour. After cooling to room temperature, the solid was filtered off and extracted with methylene chloride. Most of the methylene chloride was evaporated on a rotary evaporator and the orange powder which, precipitated was isolated by filtration and dried under reduced pressure. 12.5 g (45%) of 2c were obtained.

What is claimed is:

1. A process for preparing compounds of the formula (IV)

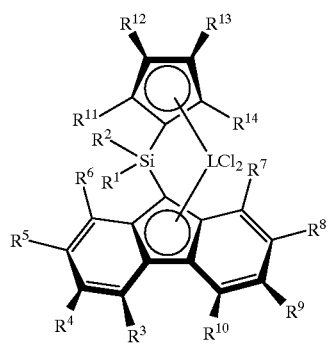

(IV)

wherein
- $R^1$, $R^2$ are identical or different $C_1$–$C_{20}$-hydrocarbon radicals,
- $R^3$, $R^4$, $R^5$, $R^6$, $R^7$, $R^8$, $R^9$, $R^{10}$ are identical or different and are each hydrogen, halogen or a $C_1$–$C_{20}$-hydrocarbon radical,
- $R^{11}$, $R^{12}$, $R^{13}$, $R^{14}$ are identical or different and are each hydrogen or a $C_1$–$C_{20}$-hydrocarbon radical, and
- L is zirconium, hafnium or titanium, comprising the measures
a) deprotonation of the compound of the formula (I)

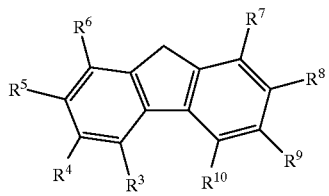

(I)

using a base,
b) reaction of the deprotonated compound from step a) with $R^1R^2SiCl_2$ to give the compound of the formula (II)

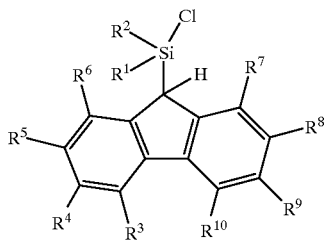

(II)

where $R^1$, $R^2$, $R^3$, $R^4$, $R^5$, $R^6$, $R^7$, $R^8$, $R^9$ and $R^{10}$ are as defined above,
c) reaction of the compound of the formula (II) obtained as described in step b) with $M^+Cp^-$ to form the compound of the formula (III)

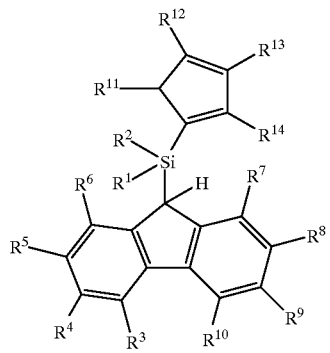

(III)

where $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are as defined above,
M is Li, Na, K, MgCl or MgBr and
Cp is a substituted or unsubstituted cyclopentadienyl radical,
d) reaction of the compound of the formula (III) with a base and addition of $LCl_4$, where L is zirconium, titanium or hafnium, to form the compound of the formula (IV)
wherein
i. the deprotonation of step a) is carried out in a mixture of one or more aromatic, aliphatic hydrocarbons and α,β-dialkoxyalkanes or α,β-dialkoxyaromatics,
ii. an alkane is added after deprotonation is complete and before the reaction with the organochlorosilane as described in step b), iii. the reaction of step d) is carried out in a mixture of one or more aromatic, aliphatic hydrocarbons and a polar aprotic solvent, with the exception of diethyl ether.

2. A process as claimed in claim 1, wherein $R^1$, $R^2$ are identical or different and are $C_1$–$C_{10}$-alkyl or $C_6$–$C_{14}$-aryl.

3. A process as claimed in claim 1, wherein $R^3$, $R^4$, $R^5$, $R^6$, $R^7$, $R^8$, $R^9$, $R^{10}$ are identical or different and are $C_1$–$C_{10}$-alkyl, $C_1$–$C_{10}$-alkenyl, $C_6$–$C_{14}$-aryl, $C_7$–$C_{12}$-alkylaryl or $C_7$–$C_{12}$-arylalkyl.

4. A process as claimed in claim 1, wherein $R^{11}$, $R^{12}$, $R^{13}$, $R^{14}$ are identical or different and are $C_1$–$C_{10}$-alkyl, $C_1$–$C_{10}$-alkenyl, $C_6$–$C_{14}$-aryl, $C_7$–$C_{12}$-alkylaryl or $C_7$–$C_{19}$-arylalkyl.

5. A process as claimed in claim 1, wherein $R^1$, $R^2$ are identical or different and are methyl, ethyl, tert-butyl or phenyl.

6. A process as claimed in claim 1, wherein $R^3$, $R^4$, $R^5$, $R^6$, $R^7$, $R^8$, $R^9$, $R^{10}$ are identical or different and are methyl, ethyl, propyl, isopropyl, n-butyl, tert-butyl, amyl, hexyl, heptyl, octyl or phenyl, where at least one radical $R^4$, $R^7$, $R^9$ and $R^{10}$ is hydrogen.

7. A process as claimed in claim 1, wherein $R^{11}$, $R^{12}$, $R^{13}$, $R^{14}$ are identical or different and are methyl, ethyl, propyl, isopropyl, n-butyl, tert-butyl, amyl, hexyl, heptyl, octyl, trimethylsilyl, triphenylmethyl, 2-methyl-2-phenylpropyl, 2,2-diphenylpropyl, 2,2-diphenylethyl or phenyl, where at least two of the radicals $R^{11}$, $R^{12}$, $R^{13}$ or $R^{14}$ are hydrogen.

8. A process as claimed in claim 1, wherein the aromatic and aliphatic hydrocarbons used are pentane, hexane and its isomers, heptane, toluene, ethylbenzene, xylene, tetrahydronaphthalene or mixtures thereof.

9. A process as claimed in claim 1, wherein the $\alpha,\beta$-dialkoxyalkanes or $\alpha,\beta$-dialkoxyaromatics used are, for example, 1,2-dimethoxyethane (DME), 2,3-dimethoxybutane, 1,2-diethoxyethane, dioxane, diethylene glycol dimethyl ether, 1,2-dimethoxybenzene, 1,2-diethoxybenzene or 2-ethoxyanisole, in particular dimethoxyethane.

10. A process as claimed in claim 1, wherein the polar aprotic solvent used is a cyclic or acyclic ether or polyether, with the exception of diethyl ether, or a tertiary amine or diamine.

* * * * *